United States Patent
Borillo et al.

(10) Patent No.: US 8,197,527 B2
(45) Date of Patent: Jun. 12, 2012

(54) EXPANDABLE IMPLANT DEVICES FOR FILTERING BLOOD FLOW FROM ATRIAL APPENDAGES

(75) Inventors: Thomas E Borillo, Plymouth, MN (US); Dean Peterson, Rogers, MN (US); Gregg S Sutton, Maple Grove, MN (US); Jeffrey Welch, New Hope, MN (US)

(73) Assignee: Atritech, Inc., Plymouth, MN (US)

( * ) Notice: Subject to any disclaimer, the term of this patent is extended or adjusted under 35 U.S.C. 154(b) by 1601 days.

(21) Appl. No.: 11/185,425

(22) Filed: Jul. 19, 2005

(65) Prior Publication Data
US 2006/0149314 A1      Jul. 6, 2006

Related U.S. Application Data

(63) Continuation of application No. 09/932,512, filed on Aug. 17, 2001, now abandoned.

(60) Provisional application No. 60/234,113, filed on Sep. 21, 2000, provisional application No. 60/234,112, filed on Sep. 21, 2000, provisional application No. 60/226,461, filed on Aug. 18, 2000.

(51) Int. Cl.
*A61F 2/06* (2006.01)
(52) U.S. Cl. ...................... 623/1.11; 606/200
(58) Field of Classification Search ............ 606/194, 606/198, 200, 213, 108, 191; 623/1.11, 1.12
See application file for complete search history.

(56) References Cited

U.S. PATENT DOCUMENTS

| | | | | | |
|---|---|---|---|---|---|
| 4,222,126 | A | * | 9/1980 | Boretos et al. | 623/2.19 |
| 5,480,410 | A | * | 1/1996 | Cuschieri et al. | 606/213 |
| 6,152,144 | A | * | 11/2000 | Lesh et al. | 128/898 |

* cited by examiner

*Primary Examiner* — Victor Nguyen
(74) *Attorney, Agent, or Firm* — Seager, Tufte & Wickhem LLC

(57) ABSTRACT

Implant devices for filtering blood flowing through the ostium of an atrial appendage have component structures one or more of which are expandable. Devices with component structures in their unexpanded state have a compact size suitable for intra-cutaneous delivery to an atrial appendage situs. The expandable component structures are expanded in situ to deploy the devices. A device may have sufficiently short axial length so that most or almost all of the device length may fit within the ostium region. An expandable component structure in the device may include a blood-permeable filter element. The device may be deployed so that this component structure covers the ostium so as to direct the blood flow to pass through the filter element. The filter elements used in the devices may have hole size distributions selected to filter out harmful-size emboli. The filter elements may be embedded in elastic material so that hole-size distributions remain substantially unaffected by expansion of the device structures. Anchors attached to a component structure engage tissue surrounding the device and maintain the devices in position. The anchors may include inflatable anchors which engage interior walls of the atrial appendage.

18 Claims, 5 Drawing Sheets

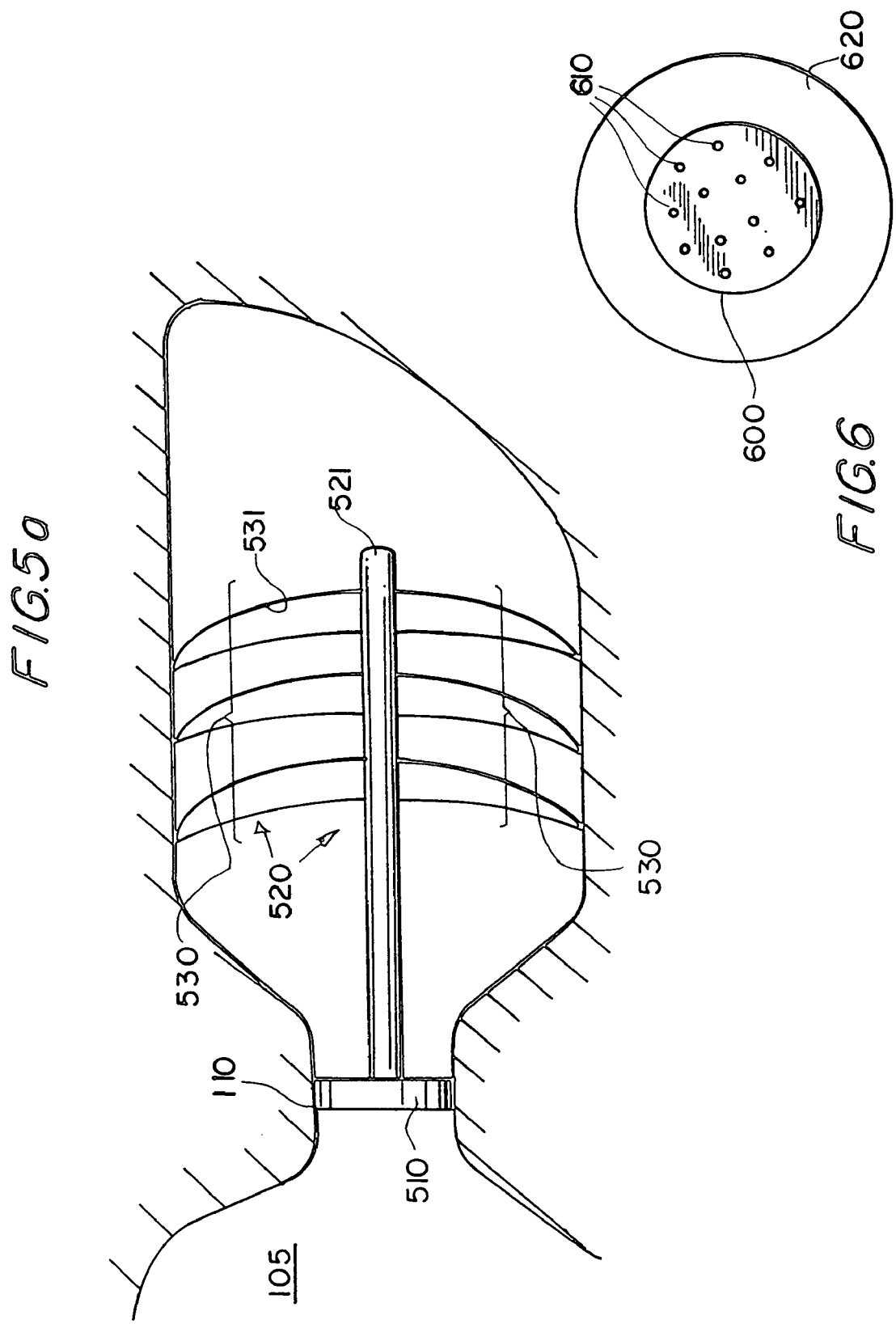

EXPANDABLE IMPLANT DEVICES FOR FILTERING BLOOD FLOW FROM ATRIAL APPENDAGES

This application is a continuation of copending U.S. application Ser. No. 09/932,512, filed Aug. 17, 2001, which claims the benefit of U.S. provisional application No. 60/226,461, filed Aug. 18, 2000, U.S. provisional application No. 60/234,112, filed Sep. 21, 2000, and U.S. provisional application No. 60/234,113, filed Sep. 21, 2000, all of which are hereby incorporated by reference in their entireties.

BACKGROUND OF THE INVENTION

1. Field of the Invention

The invention relates to implant devices that may be implanted in an atrial appendage for filtering blood flowing between the atrial appendage and an associated atrium of the heart to prevent thrombi from escaping from the atrial appendage into the body's blood circulation system.

2. Description of the Related Art

There are a number of heart diseases (e.g., coronary artery disease, mitral valve disease) that have various adverse effects on a patient's heart. An adverse effect of certain cardiac diseases, such as mitral valve disease, is atrial (or auricular) fibrillation. Atrial fibrillation leads to depressed cardiac output. A high incidence of thromboembolic (i.e., blood clot particulate) phenomena are associated with atrial fibrillation, and the left atrial appendage (LAA) is frequently the source of the emboli (particulates).

Thrombi (i.e., blood clots) formation in the LAA may be due to stasis within the fibrillating and inadequately emptying LAA. Blood pooling in the atrial appendage is conducive to the formation blood clots. Blood clots may accumulate, build upon themselves. Small or large fragments of the blood clots may break off and propagate out from the atrial appendage into the atrium. The blood clot fragments can then enter the body's blood circulation and embolize distally into the blood stream.

Serious medical problems result from the migration of blood clot fragments from the atrial appendage into the body's blood stream. Blood from the left atrium and ventricle circulates to the heart muscle, the brain, and other body organs, supplying them with necessary oxygen and other nutrients. Emboli generated by blood clots formed in the left atrial appendage may block the arteries through which blood flows to a body organ. The blockage deprives the organ tissues of their normal blood flow and oxygen supply (ischemia), and depending on the body organ involved leads to ischemic events such as heart attacks (heart muscle ischemia) and strokes (brain tissue ischemia).

It is therefore important to find a means of preventing blood clots from forming in the left atrial appendage. It is also important to find a means to prevent fragments or emboli generated by any blood clots that may have formed in the atrial appendages, from propagating through the blood stream to the heart muscle, brain or other body organs.

U.S. Pat. No. 5,865,791 (hereinafter, "the '791 patent") relates to the reduction of regions of blood stasis in the heart and ultimately reduction of thrombi formation in such regions, particularly in the atrial appendages of patients with atrial fibrillation. More specifically, the '791 patent relates to procedures and devices for affixing the atrial appendages in an orientation that prevents subsequent formation of thrombi. In the '791 patent, the appendage is removed from the atrium by pulling the appendage, placing a loop around the appendage to form a sack, and then cutting it off from the rest of the heart.

U.S. Pat. No. 5,306,234 describes a method for surgically closing the passage way between the atrium and the atrial appendage, or alternatively severing the atrial appendage.

Some recently proposed methods of treatment are directed toward implanting a plug-type device in an atrial appendage to occlude the flow of blood therefrom.

A preventive treatment method for avoiding thromboembolic events (e.g., heart attacks, strokes, and other ischemic events) involves filtering out harmful emboli from the blood flowing out of atrial appendages. Co-pending and co-owned U.S. patent application Ser. No. 09/428,008, U.S. patent application Ser. No. 09/614,091, U.S. patent application Ser. No. 09/642,291, and U.S. patent application Ser. No. 09/697,628, all of which are hereby incorporated by reference in their entireties herein, describe filtering devices which may be implanted in an atrial appendage to filter the blood flow therefrom. The devices may be delivered to the atrial appendage using common cardiac catheterization methods. These methods may include trans septal catheterization which involves puncturing an atrial septum.

Catheters and implant devices that are large may require large punctures in the septum. Large catheters and devices may damage body tissue during delivery or implantation. Damage to body tissue may cause trauma, increase recovery time, increase the risk of complications, and increase the cost of patient care. Further the atrial appendages may vary in shape and size from patient to patient.

It would therefore be desirable to provide implant devices which are small and which can be delivered by small-sized catheters to the atrial appendages. It would therefore also be desirable to provide implant devices whose size can be adjusted in situ to conform to the size of the atrial appendages.

SUMMARY OF THE INVENTION

The invention provides implant devices and methods, which may be used to filter blood flowing between atrial appendages and atrial chambers. The devices are designed to prevent the release of blood clots formed in the atrial appendages into the body's blood circulation system.

All implant devices disclosed herein have adjustable sizes. A compact or narrow size may be used for intra-cutaneous device delivery to an atrial appendage, for example, by cardiac catheterization. The devices include size-adjusting mechanisms that allow the device size to be enlarged in situ to an expanded size conforming to the dimensions of the atrial appendage.

It an embodiment of the implant device, an expanding inner structure is disposed inside a membrane tube. The inner structure has rigid components, which when the inner structure is expanded press or push sides of the membrane tube outward. The inner structure may be self-expanding or may, for example, be expanded by an inflatable balloon. When the inner structure is in a collapsed configuration, the device has a compact size suitable for delivery to and insertion in an atrial appendage, for example, by cardiac catheterization. When fully deployed for use, a closed end of the membrane tube covers the ostium of the atrial appendage. Filter elements or components built into the closed end of the membrane tube filter out harmful-size emboli from the blood flowing out of the atrial appendage. The device may be held in position by expanding the inner structure to press sides of the membrane tube against the interior walls of the atrial appendage.

Other embodiments of the implant devices may have other kinds of inflatable or expandable structures which allow the devices to have compact sizes for device delivery and which can later be enlarged in situ to make the device size conform to the dimensions of the atrial appendages.

The devices may have short axial lengths that are comparable to or are a fraction of the length of an ostium. A short-axial length device may have a thin expandable or inflatable structure. The cross-sectional shape of a thin expandable structure may, for example, resemble that of a mushroom cap, a pill box, or a doughnut-shaped tube, etc. The structure may include suitable blood-permeable filter elements for filtering harmful-size emboli from the blood flow. The filter elements may be located centrally or may be located off-center in the thin structure. When deployed the thin structure covers the ostium of an atrial appendage and directs all blood flow through the ostium to pass through the filter elements. The structure may be suitably designed to prevent unwanted flow channels (e.g., around the edges of the device) through which unfiltered blood may flow between the appendage and the atrium. The structure may have anchors attached to its outside periphery. These anchors may be pins, hooks, barbs, atraumatic bulb tips or other suitable structures for engaging wall tissue. The anchors engage the interior walls of the ostium and thereby secure the position of the deployed device. Some devices may have axial lengths that may be slightly larger than the length of an ostium. Such devices may have anchors disposed on posterior portions of the expandable structure for engaging interior wall tissue of the neck region of the atrial appendage leading to the ostium Other devices with expandable or inflatable structures may have longer axial lengths that are comparable to or are a substantial fraction of the length of an atrial appendage. A longer-axial length device may have a first structure designed to cover the ostium of an atrial appendage and filter blood flow therethrough. This first structure may optionally be expandable or non-expandable. In either case, an expandable second structure in the device may be used to help secure the device in its deployed position. The expandable second structure is generally disposed in the lumen or interior cavity of the atrial appendages. The expandable second structure may be self-expanding or may, for example, be expandable by balloon inflation. The expandable second structures may have components such as attached anchors for engaging the interior walls of the atrial appendages. These anchors may be pins, hooks, barbs, atraumatic bulb tips or other suitable structures for engaging wall tissue. The expandable second structure may additionally or alternatively include inflatable anchors. These inflatable anchors directly engage the interior walls of the atrial appendage when inflated and provide resistance to changes in the position of the deployed device.

Filter elements with predetermined hole size distributions for filtering harmful-sized emboli from the blood flow may be incorporated in the expandable implant devices. The filter elements may be configured so that their hole size distributions do not change significantly during the expansion of the device. In one configuration the filter elements are embedded in elastic membranes. These membranes are designed such that when the devices are expanded concomitant stretching of the filter element configurations due to the increase in device size is largely accommodated by the elastic membranes. The sizes of filter elements themselves and their predetermined hole size distributions remain substantially unchanged.

Further features of the invention, its nature and various advantages will be more apparent from the accompanying drawing and the following detailed description.

BRIEF DESCRIPTION OF THE DRAWINGS

FIGS. 3b and 3c are cross-sectional views illustrating exemplary shapes of the expandable structure of the implant device of FIG. 3a.

FIG. 5a is a partial cross sectional view showing an implant device with an expandable distal structure disposed in an atrial appendage. The implant device shown has a proximal structure, which may be used to cover the ostium of the atrial appendage to direct blood flow to pass through filter elements. The device is retained in position by the distal structure which has inflatable anchors in accordance with the principles of the invention.

FIG. 6 is a schematic illustration of a predetermined-size filter element having holes impervious to harmful-size emboli, and an elastic membrane attached the filter element in accordance with the principles of the invention.

DESCRIPTION OF THE PREFERRED EMBODIMENTS

Although atrial fibrillation may result in the pooling of blood in the left atrial appendage and the majority of use of the invention is anticipated to be for the left atrial appendage, the invention may also be used for the right atrial appendage and in general for placement across any aperture in the body in which blood is permitted to flow therethrough or therefrom but in which blood clots are substantially prevented from escaping from the atrial appendage and entering into the bloodstream.

The implant devices disclosed herein have adjustable sizes. A compact or narrow size is used for intra-cutaneous device delivery to the atrial appendages, for example, by cardiac catheterization. The devices include size-adjusting expansion mechanisms that allow the device size to be enlarged in situ to an expanded size. Controlled expansion may be desirable for the proper functioning of an implant device. For example, the filter elements of a device must be correctly centered or positioned across an atrial appendage ostium for the device to properly intercept and filter blood flowing out of the atrial appendage. The expansion mechanisms allow for controlled expansion of the implanted device size in situ to conform to the dimensions of the atrial appendage. Further, the expansion mechanisms may allow for the expansion to be at least partially reversed and thereby enable a physician to optimize or adjust the deployment of the device in situ. The types of implant devices disclosed herein add to variety of device types disclosed in U.S. patent application Ser. No. 09/428,008, U.S. patent application Ser. No. 09/614,091, U.S. patent application Ser. No. 09/642,291, and U.S. patent application Ser. No. 09/697,628, all incorporated in by reference herein.

Figure 1B:
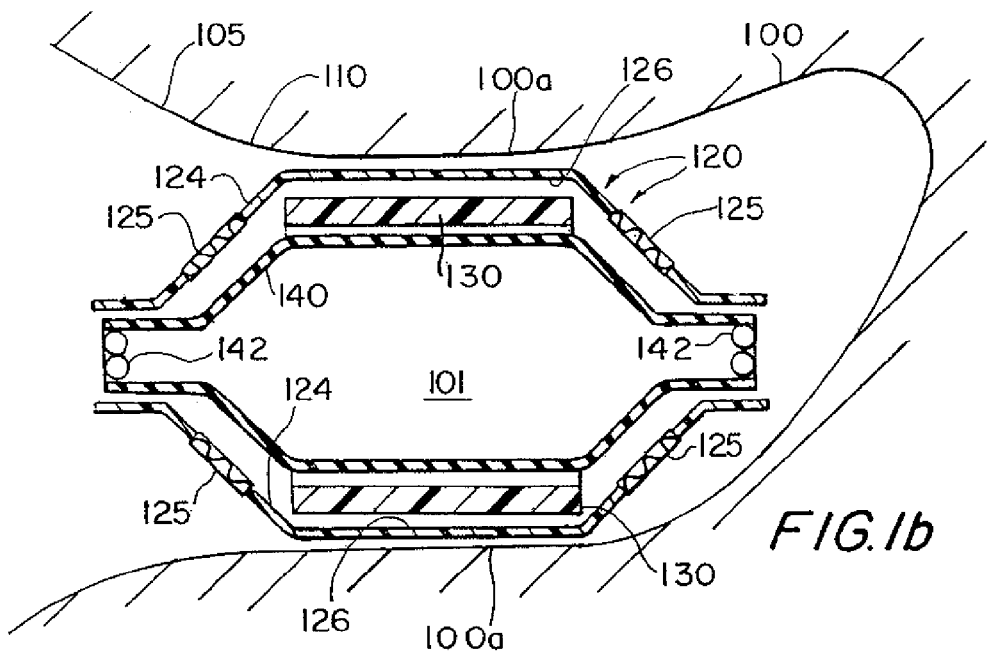
FIG. 1b is a cross sectional view showing the implant device of FIG. 1a deployed in an atrial appendage. The implant device shown has membrane tube having filter elements for filtering blood. The device is retained in position by an expanded inner structure in accordance with the principles of the invention.
Figure 1A:
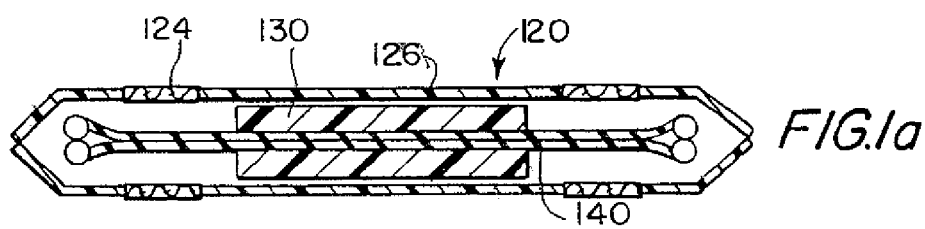
FIG. 1a is a cross sectional view showing an adjustable-size implant device at its narrow compact size suitable for delivery by cardiac catheterization in accordance with the principles of the invention.
Figure 1C:
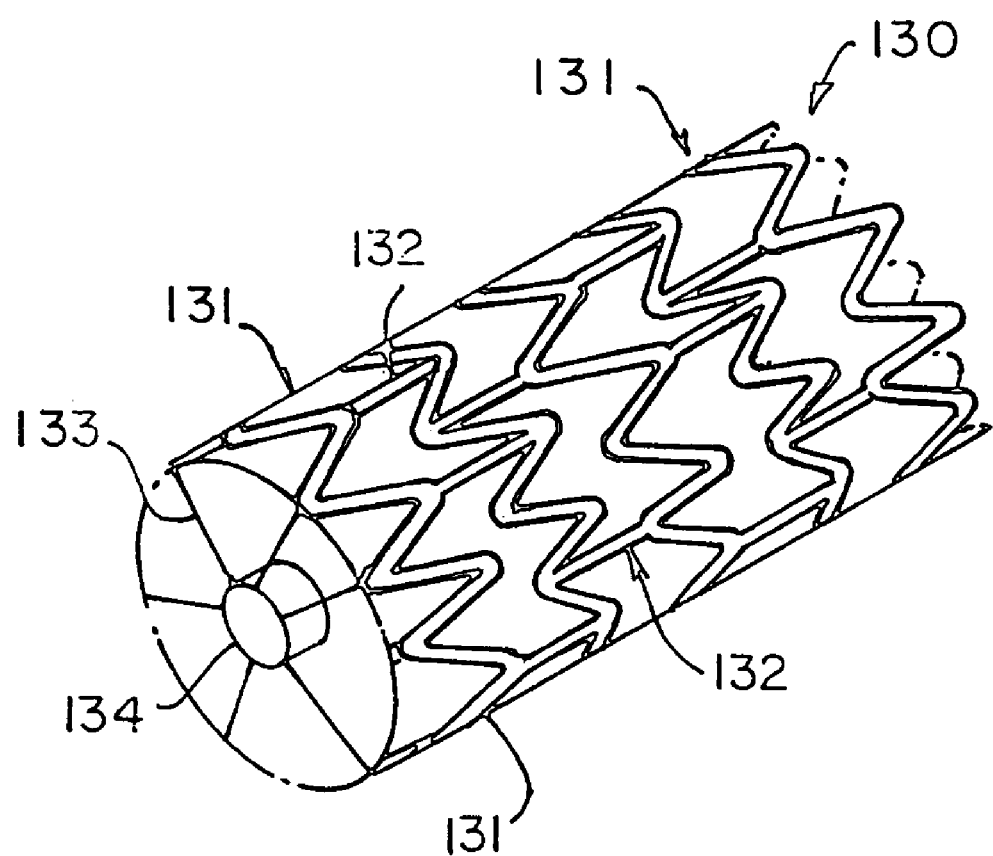
FIG. 1c is a schematic perspective view showing an exemplary expanded inner structure in its expanded configuration in accordance with the principles of the invention.

FIG. 1a shows device 101 at its compact size suitable for delivery to atrial appendage 100 (FIG. 1b) by cardiac catheterization. Device 101 has a membrane tube 120 in which an expanding structure 130 is disposed. Membrane tube 120 may be made of thin flexible materials. Expanding structure 130, in contrast, may have components which are made of more rigid material such as hard plastics or corrosion-resistant metal alloys including shape memory alloys. Expanding structure 130 has a collapsed configuration (FIG. 1a) and a larger expanded configuration (FIGS. 1b and 1c).

In both the collapsed and expanded configurations, structure 130 may have a generally cylindrical shape. Structure 130 may have a design that allows it to expand radially without any significant concomitant change in its axial length. The design of also may allow for permanent deformation, or partially or completely reversible deformation of structure 130 during its expansion. FIG. 1c schematically illustrates portions of an exemplary inner structure 130 in its expanded configuration. Structure 130 shown in FIG. 1c is similar to structures shown and described in greater detail, for example, in U.S. application Ser. No. 09/642,291. Structure 130 includes interconnected serpentine segments 131. Adjacent serpentine segments 131 are interconnected by a plurality of longitudinal struts 132. End serpentine segment 131 is connected by radial members 133 to a central hollow cylindrical ring 134. Some or all of components 130-134 may, for example, be fabricated from shape memory alloys.

Externally-initiated means may be used to change the configuration of structure 130 when it is placed in atrial appendage 100. For example, balloon 140 (e.g., placed within structure 130 through central hollow cylindrical ring 134) may be inflated to change the configuration of structure 130 from its collapsed configuration to its expanded configuration. Balloon 140 may be inflated or deflated conventionally, for example, by injecting or withdrawing suitable fluids from the body of balloon 140, respectively, through suitable elastic sealed openings, for example, valve structures 142. The elastic sealed openings such as valve structures 142 prevent uncontrolled release of fluids injected in to balloon 140.

FIG. 1b shows, for example, device 101 expanded to a suitable expanded size for permanent deployment in atrial appendage 100. Device 101 may be used to filter blood flowing out from atrial appendage 100. Device 101 has a membrane tube 120 in which an expanding structure 130 is placed. Membrane tube 120 has a generally cylindrical shape and may have one or both of its distal and proximal ends closed.

FIG. 1b shows membrane 120 having both distal and proximal closed ends 124. The membrane tube 120 can be made of biocompatible materials, such as, for example, ePFTE (e.g., Gortex®), polyester (e.g., Dacron®), PTFE (e.g., Teflon®), silicone, urethane, metal fibers, or other biocompatible polymers.

In one embodiment of device 101 at least portions of closed ends 124 serve as filter elements 125 for filtering harmful-size emboli from blood flow. Filter elements 125 are made of blood-permeable material. The remaining portions of membrane tube 125 (e.g., sides 126) may be made of blood-impervious material. The materials used to fabricate membrane tube 125 components can be any suitable bicompatible materials, such as, for example, ePFTE (e.g., Gortex®), polyester (e.g., Dacron®), PTFE (e.g., Teflon®), silicone, urethane, metal fibers, or other biocompatible polymers. The structure of the blood-permeable material used to fabricate filter elements 125 is preferably a two-dimensional screen, a cellular matrix, a woven or non-woven mesh, or the like. The structure of the blood-permeable material may also be that of a permeable metal or a mesh of fine metal fibers. Further, the blood-permeable material in filter elements 125 may be coated or covered with an anticoagulant, such as heparin, or another compound, or treated to provide antithrombogenic properties to the filter elements 125 to inhibit clogging of filter elements 125 by an accumulation of blood clots.

Filter elements 125 have holes through them for blood flow. As used herein, it will be understood that the term hole refers to an opening in the structure of a filter element which provides a continuous open channel or passageway from one side of the filter element to the other. The term pore refers to a small cavity in the material of a filter element. Cavities or pores do not provide a continuous open channel or passageway through the filter element. Partially opened surface pores, however, are an important component of surface texture which is advantageous for cellular tissue ingrowth.

The hole sizes in the blood-permeable material included in filter elements 125 may be chosen to be sufficiently small so that harmful-size emboli are filtered out from the blood flow between appendage 100 and atrium 105 (shown partially in FIGS. 1b and 1c). Yet the hole sizes may be chosen to be sufficiently large to provide an adequate flow conductivity for emboli-free blood to pass through device 101. Filter elements 125 may have hole sizes ranging, for example, from about 50 to about 400 microns in diameter. The distribution the hole sizes may be suitably chosen, for example, with regard to individual circumstances, to be larger or smaller than indicated, provided such holes substantially inhibit harmful-size emboli from passing therethrough. The open area of filter elements 125 is preferably at least 20% of the overall surface area of the closed ends 124, although a range of about 25-60% may be preferred.

The hole size distribution of the material used to make filter elements 125, described above, allows blood to flow therethrough while blocking or inhibiting the passage of thrombus, clots, or emboli formed within the atrial appendage from entering the atrium of the heart and, eventually, the patient's bloodstream.

In an alternative embodiment, substantially all of membrane tube 120 may be made of blood-permeable material suitable for filtering harmful-size emboli. Use of a single material (or a fewer number of different types of materials) in membrane tube 120 may simplify its fabrication. In this case it may be sufficient to coat or cover closed end 124 portions with an anticoagulant to prevent clogging of blood flow between atrial appendage 100 and atrium 105. Sides 126, for example, need not be coated with an anticoagulant as they are likely to be sealed in any event by atrial appendage wall tissue when device 101 is deployed in an atrial appendage, as described below.

For all embodiments of device 101, for example, as described above, when fully deployed, membrane tube 120 is held or retained in position in atrial appendage 100 so that proximal closed end 124 extends across or covers ostium 110. After initial insertion of device 101 in atrial appendage 100, expanding structure 130 is expanded, for example, by inflating balloon 140, from its initial compact size to an expanded size. Expanding structure 130 is expanded to a suitable size to press membrane tube sides 126 directly against interior walls 100a of atrial appendage 100. The direct engagement of sides 126 with interior wall tissue 100a caused by the outward pressing by structure 130 holds device 101 provides a degree of resistance to movement of device 101 within atrial appendage 100 and holds device 101 in a substantially fixed position. However, this resistance to movement at least initially during the implant procedure may be reversed to allow repositioning of device 101 if necessary or desirable. The reversal may be complete or partial corresponding to the elastic deformation characteristics of structure 130. The reversal may be accomplished, for example, by deflation of balloon 140. Later, regenerative tissue growth, for example, of endothelial or endocardial tissue, conforming to the outer surface textures of sides 126 may bind sides 126 and provide additional securement of fully deployed device 101. This tissue growth binding may, for example, involve tissue ingrowth into partially-open surface pores of the material of sides 126, or, for example, tissue ingrowth into holes in blood-permeable material in the case where sides 126 are made of blood-permeable material having holes. This tissue growth, in conjunction with the outward pressure provided by inner structure 130, may provide additional means of reducing flow leakage about the periphery of device 101.

In some implant procedures it may be desirable to leave balloon 140 in situ, for example, in a deflated state. In other implant procedures it may be desirable to physically remove balloon 140 after device 101 has been secured in appendage 100. As necessary or desired, balloon 140 may be removed from the patient's body using conventional catheterization techniques. Balloon 140 may be withdrawn from tube 120 through suitable self-sealing openings in closed ends 124. A suitable self-sealing opening may be of the type formed by overlapping membrane flaps (e.g., flaps 124 FIG. 1b). Other types of conventional self-sealing openings such as those formed by elastic O-ring structures (not shown) also may be used.

Figure 2:
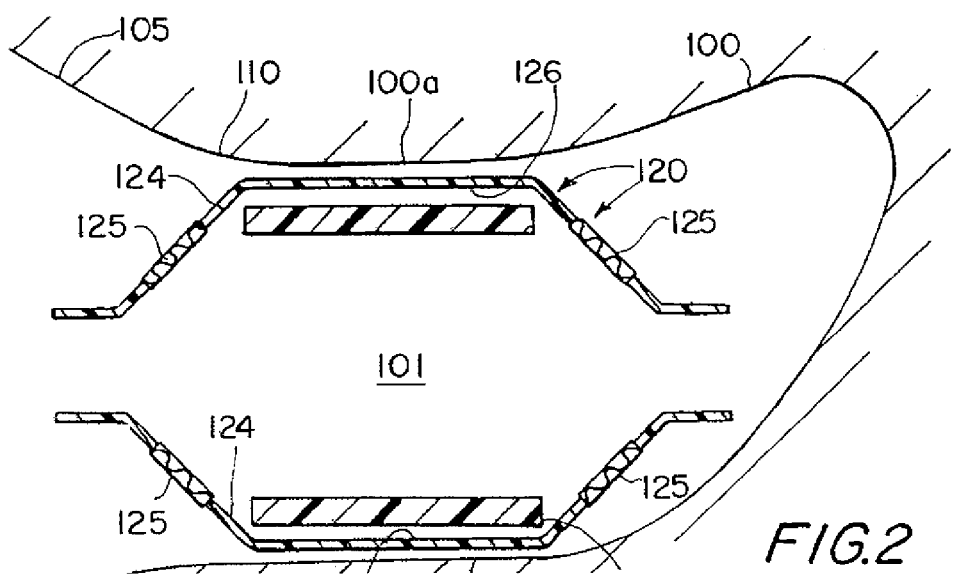
FIG. 2 is a partial sectional view showing another implant device deployed in an atrial appendage. The implant device shown has filter elements for filtering blood and is retained in position by a self-expanding inner structure in accordance with the principles of the invention.

In further embodiments of device 101, expanding inner structure 130 may be a self-expanding structure. Structure 130 may have suitable biasing means, for example, springs or other elastic components, which change the configuration of structure 130 from its as-implanted collapsed configuration to its expanded configuration after device 101 has been implanted. Self-expanding structure 130 also may, for example, have components made from shape memory alloys (e.g., Nitinol®). The shape memory alloy components may be preformed to have a shape corresponding to the expanded configuration of structure 130. The performed components may be bent or compressed to form structure 130 in its collapsed configuration. After device implantation, heating or changing temperature induces the bent or compressed the shape memory alloy components to automatically revert to their performed shapes corresponding to the expanded configuration of structure 130. FIG. 2 shows, for example, device 101 expanded by self-expanding structure 200 to a suitable expanded size for permanent deployment in an atrial appendage 100.

Other embodiments of the implant devices may have other kinds of inflatable or expandable structures, which allow the devices to have compact sizes for device delivery, and which can later be enlarged in situ to make the device sizes conform to the dimensions of the atrial appendages. An implant device of these embodiments may have one or more component structures or substructures. One or more of the component structures or substructures in a device may be expandable or inflatable. A first type of these component structures or substructures may include blood-permeable filter elements, and, for example, serve to filter harmful size emboli from the blood flow. A second type of the component structures or substructures may include anchoring elements, and, for example, serve to retain the deployed device in position. It will be understood that neither component types are contemplated within the invention as necessarily having mutually exclusive functions. Neither type is restricted to having only filter elements or only anchoring elements. A single component structure may serve both to filter blood flow and to hold the deployed device in position.

Different embodiments of devices having one or more of these types of component structures or substructures may have correspondingly different axial lengths spanning a wide range of values. At the upper end of the range, devices may have axial lengths that are comparable to or are a significant fraction of the length of an atrial appendage. Toward the lower end of the range, devices may have axial lengths that are comparable to or are a fraction of the length of the ostium and the neck region of the atrial appendage leading to the ostium.

Figure 3A:
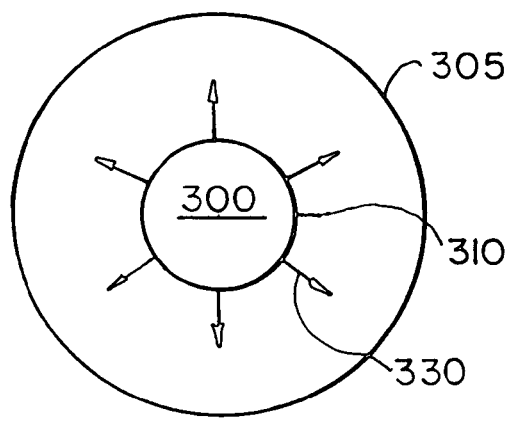
FIG. 3a is a schematic illustration of an as-delivered implant device positioned within an ostium. The device has a thin expandable structure which may be used to cover the ostium of an atrial appendage so that blood flow between the appendage and the atrium is constrained to pass through filter elements in the device in accordance with the principles of the invention.
Figure 3B:
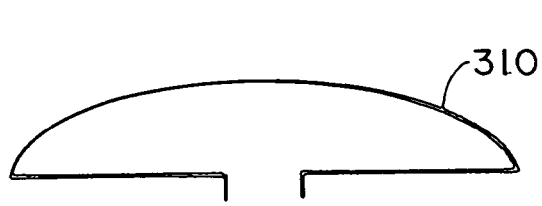
Figure 3C:
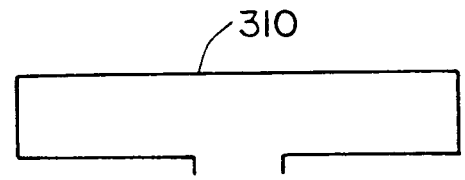

A device embodiment having a short axial length suitable for deployment fully within an ostium is illustrated in FIGS. 3a, 3b, 3c, and 4. Device 300 has a thin expandable or inflatable structure 310. FIG. 3a schematically shows device 300 as delivered for deployment positioned within ostium 305. Structure 310 when expanded may have a shape, for example, resembling a mushroom cap (FIG. 3b), a pill box (FIG. 3c), a doughnut-shaped tube, or any other shape suitable for engaging ostium 305.

Expandable structure 310 may be fabricated from membranes or fabrics made of bicompatible materials, such as, for example, ePFTE (e.g., Gortex®), polyester (e.g., Dacron®), PTFE (e.g., Teflon®), silicone, urethane, metal fibers, or other biocompatible polymers. Expandable structure 310 includes filter elements for filtering harmful-size emboli (not shown). Structure 310 may include non-expanding portions made of blood-permeable membrane or fabric suitable for filtering harmful-size emboli (not shown). The non-expanding portions may, for example, in the case where structure 310 has an expandable doughnut shape extend across the central region of the doughnut shape. Structure 310 may also include access openings or fixtures for attaching catheters or other delivery devices (not shown). Anchors 330 are attached to the outer periphery of expandable structure 330. Anchors 330 may, for example, be attached to an outer rim toward the posterior of expandable structure 330. Anchors 330 may be pins, hooks, barbs, wires with atraumatic bulb tips or other suitable structures for engaging tissue. Device 300 is secured in position relative to ostium 305 when anchors 330 engage surrounding ostium wall tissue.

Figure 4:
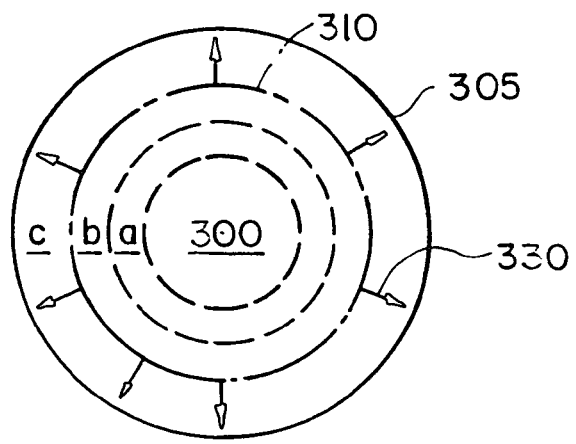
FIG. 4 schematically illustrates the increase in size of the implant device of FIG. 3a as its expandable structure is being inflated in accordance with the principles of the invention.

Device 300 may be suitably deployed to filter blood flowing through ostium 305 by extending expandable structure 310 across ostium 305. Expandable structure 320 may be self-expanding (e.g., like structure 130 FIG. 2). Alternatively, expandable structure 310 may include externally-initiated mechanical means for expansion (e.g., like balloon 140 FIG. 1b). FIG. 4 schematically illustrates the increase in size of device 300 as expandable structure 310 is being inflated. FIG. 4 shows device 300 increasing from an initial size a to an intermediate size b, and then to a size c. As device 300 size increases attached anchors 330 move radially outward toward the interior walls of ostium 305. When structure 310 is sufficiently expanded, anchors 330 engage surrounding interior wall tissue and secure device 300 in position.

FIG. 5a shows an implant device 500 having an axial length which is comparable or a significant fraction of the length of atrial appendage 100. Device 500 has two component substructures, i.e., proximal structure 510, and distal structure 520. Proximal structure 510 may be used to cover ostium 110 of atrial appendage 100. Proximal structure 510 includes blood-permeable filter elements which filter the blood flow through ostium 110. Proximal structure 510 may be made of a suitable fabric made from bicompatible materials, such as, for example, ePFTE (e.g., Gortex®), polyester (e.g., Dacron®), PTFE (e.g., Teflon®), silicone, urethane, metal fibers, or other biocompatible polymers. Proximal structure 510 may be an expandable structure, which may, for example, be similar to expandable structure 310 described above with reference to FIGS. 3a, 3b and 3c. Alternatively, proximal structure 510 may be a structure which is not expandable or inflatable. Non-inflatable structure 510 may, for example, be any one of the structures for covering ostium 110 described in U.S. patent application Ser. No. 09/428,008, U.S. patent application Ser. No. 09/614,091, U.S. patent application Ser. No. 09/642,291, and U.S. patent application Ser. No. 09/697,628, all incorporated by reference herein.

In either case, structure 510 is retained in position extending across ostium 110 by use of attached distal structure 520. Distal structure 520 is inflatable and has one or more anchor sets 530 attached to an axial portion or shank 521. Each of the anchor sets 530 has a suitable number of inflatable anchors 531 designed to engage the interior walls of atrial appendage 100. Inflatable anchors 531 in a set 530 may be attached to axial portion 521 along a radial circumference at a suitable distance away from proximal cover 510 (not shown). Alternatively, inflatable anchors 531 in a set 530 may be attached to axial portion 521 along an axial length thereof, for example, as illustrated in FIG. 5a. Other distributions of anchors 531 also may be used. For example, anchors 531 may be attached to axial portion 521 in a spiral pattern. Distal structure 520 including anchor sets 530 may be made of a suitable fabric made of bicompatible materials, such as, for example, ePFTE (e.g., Gortex®), polyester (e.g., Dacron®), PTFE (e.g., Teflon®), silicone, urethane, metal fibers, or other biocompatible polymers.

Device 500 is at its compact size suitable for intra-cutaneous delivery when distal structure 520 is deflated, and when proximal structure 510 deflated or suitably folded according to whether proximal structure 510 is an expanding or a non-expanding structure. In an implant procedure, device 500 in its compact size may be delivered to atrial appendage 100, for example, by cardiac catheterization. When fully deployed, device 500 is positioned so that proximal structure 510 appropriately extends across ostium 110. Distal structure 520 is disposed to the interior of atrial appendage 100. Distal structure 520 is inflated by suitable means so that inflated anchors 531 engage and press against the interior walls of atrial appendage 100. The friction between outwardly pressing anchors 531 and the atrial appendage walls retains device 500 in its desired fully deployed position. The suitable means for inflating structure 520 may, for example, involve injection of fluids into structure 520 through suitable openings (not shown). The openings may have suitable valved seals preventing uncontrolled release or leakage of the inflating fluids.

In another device embodiment, a single inflatable structure may provide the functions of both the distal and proximal structures described above. Such a device may have a sufficiently short axial length so that all or almost all of the device may fit within the ostium or ostium region of an atrial appendage Anterior portions of the device may be used cover the ostium in order to direct blood flow between the atrial appendage and the atrial chamber through filter elements. Attached anchors may be distributed on at least part of the exterior surface area of posterior portions of the device. The anchors may be pins, hooks, barbs, wires with atraumatic bulb tips or other suitable structures for engaging tissue. The single inflatable structure may be self-expanding or may expand in response to externally-initiated means. When the device is expanded the anchors attached to its posterior portions engage the rear walls of the ostium and/or possibly the interior walls of the neck region of the atrial appendage close to the ostium. The device may be fabricated using suitable membranes or fabrics made of biocompatible materials, for example, such as those mentioned earlier. Further, the biocompatible materials may have, for example, any of the structures mentioned earlier (e.g., cellular matrix, wire mesh, etc.).

Figure 5B:
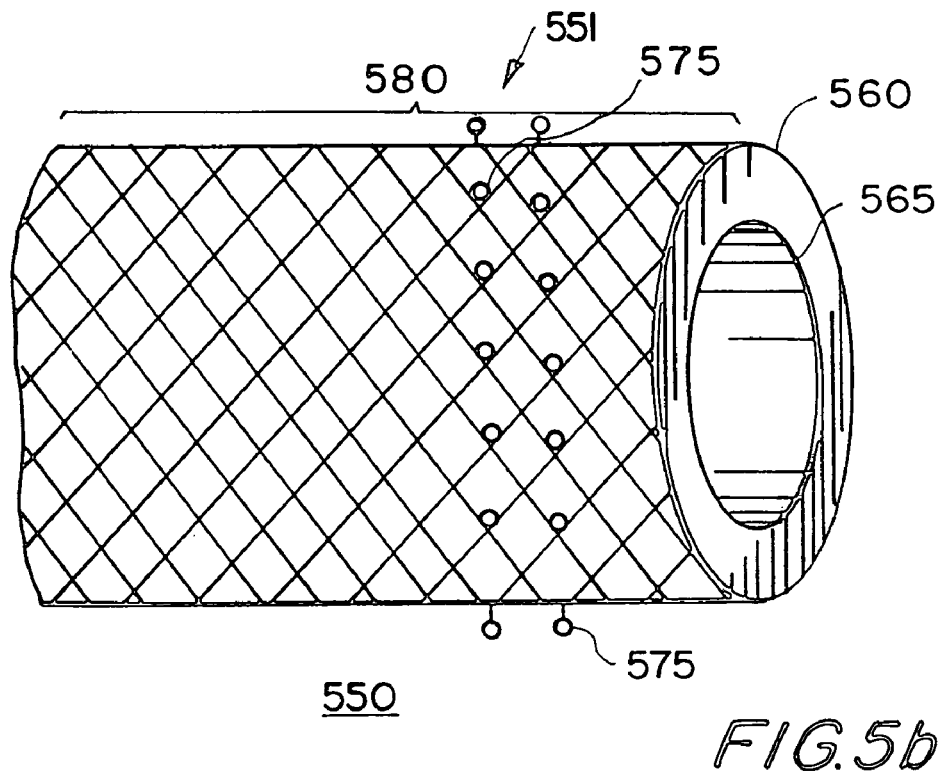
FIG. 5b is a side elevational view showing another implant device with expandable structures in which a single expanding structure provides the functions of both the proximal and distal structures shown in FIG. 5b, in covering the ostium and in securing the position of the device, in accordance with the principles of the invention.
Figure 5C:
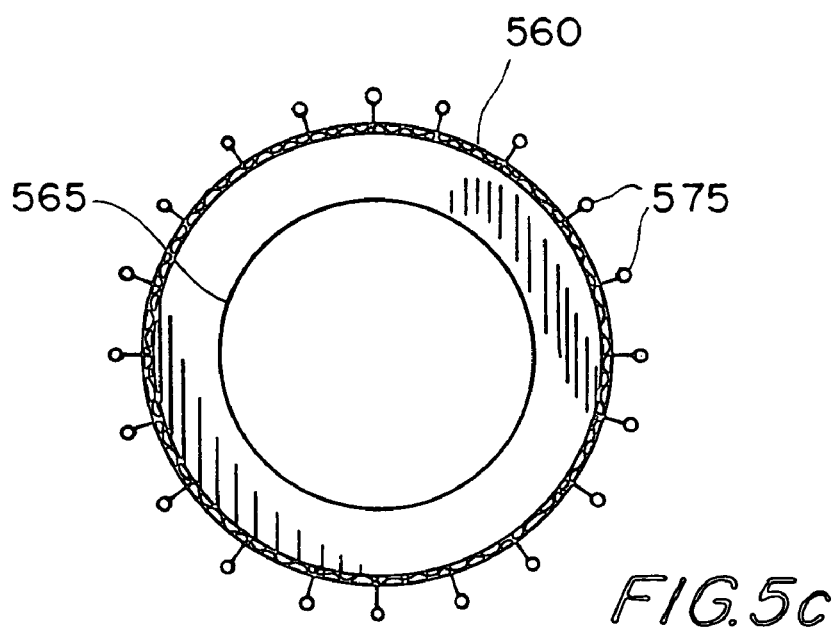
FIG. 5c is a plan view of the implant device shown in FIG. 5b.

An exemplary implant device 550 most or almost all of which may fit within the ostium of an atrial appendage is illustrated in FIG. 5b and FIG. 5c. These two FIGS. show side elevational and top plan views of device 550, respectively. Device 550 like device 300 (FIG. 3a) has a single component structure, i.e., expandable structure 551. Expandable structure 551 includes anterior portion 560 and posterior portion 570. The axial length of device 550 may be comparable to or slightly larger than the length of the ostium. Device 550 with an axial length slightly larger than the length of the ostium, when deployed, may extend into the neck region of the atrial appendage close to the ostium.

FIG. 5b shows device 550 at an expanded size at which it may be deployed in the ostium. Anterior portion 560 may be fabricated from an elastic membrane and include suitable filter element 565 for filtering harmful-size emboli from the blood flow. Anterior portion 560 may include suitable openings or fixtures for attaching catheters or other delivery devices (not shown). Anterior portion 560 is used to cover the ostium to ensure that all blood flow through the ostium passes through filter element 565. Posterior portion 570 may, for example, be formed of a wire mesh (as shown), a braided or woven fabric, or a short segment of sheet material tube. Posterior portion 570 may have suitable radial dimensions conforming to the ostium dimensions. FIG. 5c shows, for example, a cylindrical posterior portion 570 having a substantially constant diameter cross-section along its axial length. Alternatively, cylindrical posterior portion 570 may be flared with its diameter increasing along its axial length to match changes in the ostium diameter, for example, as the ostium merges into the neck region of the atrial appendage (not shown).

As shown in FIG. 5b, posterior portion 570 has barbs 575 distributed over a part of its exterior surface area close to anterior portion 560. Alternatively, barbs 575 may be distributed over all of the exterior surface area. When device 550 is positioned and expanded in an ostium, barbs 575 engage the surrounding ostium walls (and possibly neck region walls) to secure device 550 in position.

Posterior portion 570 may optionally have suitable elastic deformation properties that cause portion 570 to recoil slightly in size from its largest expanded size. Such suitable deformation properties may be obtained by design, for example, by choice of fabrication materials with suitable elastic properties. The size recoil of device 550 causes barbs 575 which have engaged the ostium and/or neck region walls during the expansion of device 550 to pull back and draw the walls closer to device 550. The expandable structures in other device embodiments including those described earlier (e.g., FIGS. 1-4, FIG. 5a) also may have similar size recoil characteristics which cause attached anchors to engage and draw surrounding wall tissue closer to the devices.

The various expandable implant devices (e.g., those described above with reference to FIGS. 1-5) may have filter elements for filtering harmful-size emboli out of the blood flowing out from the atrial appendages into the atria. For effective filtering, the filter elements should have appropriate hole size distributions which filter out harmful-size emboli. Since the implant devices are likely to be expanded to different sizes in use, for example, to conform to the varying dimensions of individual atrial appendages, the filter elements are configured so that their hole size distributions do not change significantly during the expansion of the device.

For example, FIG. 6 shows one configuration of filter element 600 in which the size distribution of holes 610 does not change significantly during device deployment. In the configuration shown, filter element 600 is attached to elastic membrane 620. Filter element 600 and elastic membrane 620 may, for example, be made of a suitable membrane or fabric composed of bicompatible materials, such as, for example, ePFTE (e.g., Gortex®), polyester (e.g., Dacron®), PTFE (e.g., Teflon®), silicone, urethane, metal fibers, or other biocompatible polymers. Filter 600 may have hole sizes ranging, for example, from about 50 to about 400 microns in diameter, suitable for filtering harmful-sized emboli. This range of hole size distribution may be adequate to make filter element 600 impervious to harmful-sized emboli, and yet provide enough permeability for blood to flow through element 600. The hole size distribution may be selected, for example, by selecting the open weave density of the fabric used to make filter 600. Alternatively, for example, for filter elements made of solid sheet material, other techniques such as laser drilling may be used for making small diameter holes.

Filter element 600 and elastic membrane 620 are constructed so that the former component is substantially less elastic than the latter component. This difference in elasticity may be obtained, for example, by using the same kind of material to make both components, but by making filter element 600 substantially thicker than elastic membrane 620. Alternatively, elastic membrane 620 and filter 600 may be made of two different kinds of materials that have different elastic properties. The two different material components may be bonded or glued together.

Filter element 600 and elastic membrane 620 may be incorporated in various types of implant device structures, for example, membrane tube 120 FIG. 1a, expandable structure 310 FIG. 3a, proximal structure 510 FIG. 5a, and anterior portion 560 FIG. 5b. When the device incorporating these two components is expanded, most of the concomitant stretching of the filter configuration due to the increase in device size is accommodated by the stretching of elastic membrane 620 leaving the size of filter element 600 substantially unchanged from its predetermined value.

It will be understood that the foregoing is only illustrative of the principles of the invention, and that various modifications can be made by those skilled in the art without departing from the scope and spirit of the invention. It will be understood that terms like "distal" and "proximal", "anterior" and "posterior", and other directional or orientational terms are used herein only for convenience, and that no fixed or absolute orientations are intended by the use of these terms.

What is claimed is:

1. A device for filtering blood flowing through the ostium of an atrial appendage, comprising:
    a membrane tube having at least a first closed end wherein said first closed end comprises a blood-permeable filter and a second closed end, said second closed end comprises a blood permeable filter; and
    an expandable structure disposed in said tube, said structure having a collapsed configuration and an expanded configuration,
    wherein said device is insertable in said appendage while said expandable structure is in said collapsed configuration, and wherein when said expandable structure is in said expanded configuration said closed end covers the ostium of said atrial appendage and portions of said membrane tube are pressed outwards against the interior walls of said atrial appendage anchoring said device therein.

2. The device of claim 1 wherein said membrane tube has a substantially cylindrical shape.

3. The device of claim 1 wherein said expandable structure is self-expanding.

4. The device of claim 1 wherein said expandable structure expands from said collapsed configuration to said expanded configuration by means of an inflatable balloon.

5. The device of claim 4 wherein said first closed end further comprises a self-sealing opening for withdrawing said inflatable balloon.

6. The device of claim 5 wherein said self-sealing opening comprises an elastic ring.

7. The device of claim 5 wherein said self-sealing opening comprises overlapping membrane flaps.

8. The device of claim 1 wherein said membrane tube comprises elastomeric material.

9. The device of claim 1 wherein said membrane tube comprises braided material.

10. The device of claim 1 wherein said membrane tube comprises woven material.

11. The device of claim 1,
    wherein said expandable membrane stretches as said cover is deployed and allows said predetermined size to remain substantially unchanged.

12. The device of claim 11 wherein said filter element comprises holes substantially impervious to harmful-size emboli.

13. The filter of claim 11 wherein said filter element is made of material which is less elastic than said expandable membrane.

14. A method for filtering blood flowing through the ostium of an atrial appendage, comprising:
    providing a device comprising a membrane tube having at least a first closed end wherein said first closed end comprises a blood-permeable filter and a second closed end, said second closed end comprises a blood permeable filter;
    inserting said device in said appendage;
    positioning said closed end to cover said ostium; and
    anchoring said device in said atrial appendage.

15. The method of claim 14 wherein said anchoring comprises pressing sides of said tube outward against the interior walls of said atrial appendage.

16. The method of claim 14 wherein said providing a device further comprises disposing an expandable structure in said membrane tube, wherein said inserting further comprises placing said device in said atrial appendage while said expandable structure is in a collapsed configuration, and wherein said positioning and said anchoring comprise expanding said expandable structure to an expanded configuration.

17. The method of claim 16 wherein said expanding comprises using an inflatable balloon.

18. The method of claim 17 further comprising deflating and withdrawing said balloon from said atrial appendage after said device is anchored in said atrial appendage.

* * * * *